US010902741B2

(12) United States Patent
Rubinstein et al.

(10) Patent No.: US 10,902,741 B2
(45) Date of Patent: Jan. 26, 2021

(54) EXERCISE FEEDBACK SYSTEM FOR MUSCULOSKELETAL EXERCISES

(71) Applicant: Physera, Inc., Palo Alto, CA (US)

(72) Inventors: Yigal Dan Rubinstein, Los Altos, CA (US); Cameron Marlow, Menlo Park, CA (US); Todd Riley Norwood, Redwood City, CA (US); Jonathan Chang, San Francisco, CA (US); Shane Ahern, Belmont, CA (US); Daniel Matthew Merl, Livermore, CA (US)

(73) Assignee: Physera, Inc., Palo Alto, CA (US)

( * ) Notice: Subject to any disclaimer, the term of this patent is extended or adjusted under 35 U.S.C. 154(b) by 338 days.

(21) Appl. No.: 15/928,019

(22) Filed: Mar. 21, 2018

(65) Prior Publication Data
US 2019/0295436 A1 Sep. 26, 2019

(51) Int. Cl.
G09B 19/00 (2006.01)
A61B 5/00 (2006.01)
(Continued)

(52) U.S. Cl.
CPC ........ *G09B 19/0038* (2013.01); *A61B 5/0013* (2013.01); *A61B 5/0077* (2013.01);
(Continued)

(58) Field of Classification Search
CPC ..... A61B 5/0013; A61B 5/1128; A61B 5/486; A61B 5/1123; A61B 5/0022; A61B 5/1121; A61B 5/1114; A61B 5/0077; A61B 5/7425; A61B 5/1116; A61B 5/742; A61B 5/7267; A61B 2503/10; A61B 2505/09; A61B 2576/00; G16H 50/20; G16H 20/30; G16H 40/63; A63B 24/0062; A63B 24/0006; A63B 71/06; A63B 2220/62; A63B 2220/807; A63B 2024/0015; A63B 2220/806; A63B 2024/0009; G09B 19/0038; G09B 5/14
See application file for complete search history.

(56) References Cited

U.S. PATENT DOCUMENTS

2004/0010420 A1 1/2004 Rooks
2004/0122310 A1* 6/2004 Lim .................... A61B 8/0816
600/426
(Continued)

Primary Examiner — Nathan Hillery
(74) Attorney, Agent, or Firm — Fenwick & West LLP

(57) ABSTRACT

An exercise feedback system receives exercise data captured by client devices of users performing musculoskeletal exercises. The exercise feedback system may provide captured images to a client device of a physical trainer (PT) who remotely provides feedback on the users' exercise performances, for example, by labeling images as indicative of proper or improper musculoskeletal form. A PT may track multiple users using a central feed, which includes content displayed in an order based on ranking of users by a model. Additionally, the exercise feedback system may provide an augmented reality (AR) environment. For instance, an AR graphic indicating a target musculoskeletal form for an exercise is overlaid on a video feed displayed by a client device. Responsive to detecting that a user's form is aligned to the AR graphic, the exercise feedback system may notify the user and trigger the start of the exercise.

20 Claims, 12 Drawing Sheets

(51) Int. Cl.
   *A63B 24/00* (2006.01)
   *A63B 71/06* (2006.01)
   *G09B 5/14* (2006.01)

(52) U.S. Cl.
   CPC ............ *A61B 5/486* (2013.01); *A61B 5/7267* (2013.01); *A61B 5/7425* (2013.01); *A63B 24/0006* (2013.01); *A63B 24/0062* (2013.01); *A63B 71/06* (2013.01); *G09B 5/14* (2013.01); *A61B 2503/10* (2013.01); *A61B 2505/09* (2013.01); *A61B 2576/00* (2013.01); *A63B 2024/0009* (2013.01); *A63B 2024/0015* (2013.01); *A63B 2220/62* (2013.01); *A63B 2220/806* (2013.01); *A63B 2220/807* (2013.01)

(56) References Cited

U.S. PATENT DOCUMENTS

| | | |
|---|---|---|
| 2007/0118406 A1 | 5/2007 | Killin et al. |
| 2007/0139362 A1 | 6/2007 | Colton et al. |
| 2007/0179816 A1 | 8/2007 | Lemme |
| 2009/0297012 A1* | 12/2009 | Brett ................ G06K 9/6263 382/132 |
| 2009/0306496 A1* | 12/2009 | Koo .................... A61B 5/055 600/417 |
| 2011/0004126 A1* | 1/2011 | Einav ................. G06Q 50/24 600/595 |
| 2011/0270135 A1 | 11/2011 | Dooley et al. |
| 2013/0123667 A1* | 5/2013 | Komatireddy .......... G06T 7/20 600/595 |
| 2013/0138734 A1 | 5/2013 | Crivello et al. |
| 2013/0281888 A1 | 10/2013 | Bender et al. |
| 2013/0316316 A1 | 11/2013 | Flavell et al. |
| 2013/0325493 A1* | 12/2013 | Wong ..................... G16H 50/20 705/2 |
| 2014/0088985 A1 | 3/2014 | Grant et al. |
| 2014/0088990 A1 | 3/2014 | Nawana et al. |
| 2014/0172460 A1* | 6/2014 | Kohli .................. G06F 19/3481 705/3 |
| 2014/0221181 A1* | 8/2014 | Pickett ................. A61B 5/4824 482/139 |
| 2014/0272891 A1* | 9/2014 | Saladino ................ G09B 5/02 434/350 |
| 2014/0322687 A1 | 10/2014 | Wong et al. |
| 2015/0072327 A1* | 3/2015 | Beaulieu ............ G06F 19/3481 434/257 |
| 2015/0196804 A1* | 7/2015 | Koduri ..................... G06T 7/20 482/8 |
| 2015/0302766 A1* | 10/2015 | Oberlander .......... G09B 19/003 434/247 |
| 2016/0005320 A1* | 1/2016 | deCharms ............ A61B 8/0808 434/236 |
| 2016/0171683 A1* | 6/2016 | Lee ........................ G16H 50/70 382/128 |
| 2016/0300347 A1* | 10/2016 | Dunn ........................ G06T 7/60 |
| 2017/0100637 A1* | 4/2017 | Princen .............. G06K 9/00342 |
| 2017/0119281 A1* | 5/2017 | Herrmann ............ A61B 5/0082 |
| 2017/0245759 A1* | 8/2017 | Jain ........................ A61B 5/087 |
| 2018/0036591 A1* | 2/2018 | King .................. G06F 19/3481 |
| 2018/0184947 A1* | 7/2018 | Richards .............. A61B 5/1121 |
| 2018/0256092 A1 | 9/2018 | Obma et al. |
| 2018/0279919 A1* | 10/2018 | Bansbach ............ A61B 5/1121 |
| 2018/0304118 A1 | 10/2018 | French |
| 2018/0330810 A1* | 11/2018 | Gamarnik .............. G16H 50/50 |
| 2018/0361203 A1* | 12/2018 | Wang ................ A63B 24/0075 |
| 2019/0148001 A1* | 5/2019 | Hughes .................. G16H 20/40 702/19 |
| 2019/0228848 A1 | 7/2019 | Saliman |
| 2020/0051446 A1 | 2/2020 | Rubinstein et al. |

\* cited by examiner

```
┌─────────────────────────────────────┐
│ Provide an AR graphic indicating a  │
│ target musculoskeletal form for     │
│ display on a client device of a user│
│                1110                 │
└─────────────────────────────────────┘
                  │
                  ▼
┌─────────────────────────────────────┐
│ Receive video data captured by a    │
│ camera of the client device         │
│                1120                 │
└─────────────────────────────────────┘
                  │
                  ▼
┌─────────────────────────────────────┐
│ Determine a musculoskeletal form of │
│ the user by processing the video data│
│                1130                 │
└─────────────────────────────────────┘
                  │
                  ▼
┌─────────────────────────────────────┐
│ Determine a level of similarity     │
│ between the musculoskeletal form and│
│ the target musculoskeletal form     │
│                1140                 │
└─────────────────────────────────────┘
                  │
                  ▼
┌─────────────────────────────────────┐
│ Start an exercise program and provide│
│ a notification for display on the   │
│ client device responsive to         │
│ determining that the level of       │
│ similarity satisfies a criteria     │
│                1150                 │
└─────────────────────────────────────┘
```

FIG. 11

EXERCISE FEEDBACK SYSTEM FOR MUSCULOSKELETAL EXERCISES

CROSS REFERENCE TO RELATED APPLICATIONS

This application is related to U.S. application Ser. No. 15/928,202, entitled "Customizing Content for Musculoskeletal Exercise Feedback," filed on Mar. 21, 2018; and is also related to U.S. application Ser. No. 15/928,024, entitled "Augmented Reality Guided Musculoskeletal Exercises," filed on Mar. 21, 2018. Both of the foregoing applications are incorporated by reference herein in their entirety for all purposes.

BACKGROUND

This disclosure generally relates to exercises for the musculoskeletal system, and more specifically to providing feedback on musculoskeletal form for exercises.

Physical exercise helps maintain the musculoskeletal system of the body and prevent conditions including chronic pain, arthritis, osteoporosis, or injury, among others. Individuals may seek feedback regarding musculoskeletal exercises from personnel such as physical therapists or electronic resources, for example, online guides, applications, or videos. However, existing systems and resources for exercise feedback do not provide individuals with customized evaluations on their exercises outside of in-person sessions with physical therapists, for instance, feedback indicating whether the individuals are performing exercises with proper musculoskeletal form per repetition. It would be desirable for individuals to receive personalized physical therapy regardless of the exercise setting, which may encourage users to perform more exercises at home or work, and thus promote a healthy musculoskeletal system or overall fitness. Moreover, it is challenging for an individual to identify a physical therapist who will provide reliable feedback that is customized to the individual's health goals or conditions.

SUMMARY

An exercise feedback system receives exercise data captured by client devices of users performing musculoskeletal exercises. Exercise data may include image data, video data, depth information, or other types of exercise-related information. A user may position a client device, for example, a smartphone, such that a field of view of a camera of the client device can capture image, video, or depth information of the user performing an exercise. The exercise feedback system transmits captured exercise data to another client device of a physical trainer (PT) who may remotely provide feedback on the user's exercise performance. For example, the PT may classify or label certain images as indicative of proper or improper musculoskeletal form for an exercise. In addition, the exercise feedback system may generate scores to evaluate PTs by comparing their classifications of images to feedback provided by other PTs or to reference data, for example, a predetermined target musculoskeletal form for a given exercise in 2D or 3D. The exercise feedback system may use the scores, along with user preferences, to recommend candidate PTs to a user. In some embodiments, the exercise feedback system performs AB tests using control and test populations of users, which may be used for clinical trials to evaluate musculoskeletal exercises.

BRIEF DESCRIPTION OF DRAWINGS

FIG. 7 is a diagram of an example user interface layout including aggregate information for multiple users of the exercise feedback system according to an embodiment.

FIG. 11 is a flowchart illustrating a process for starting an exercise program using an augmented reality graphic according to one embodiment.

DETAILED DESCRIPTION

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example System Environment

Figure 1:
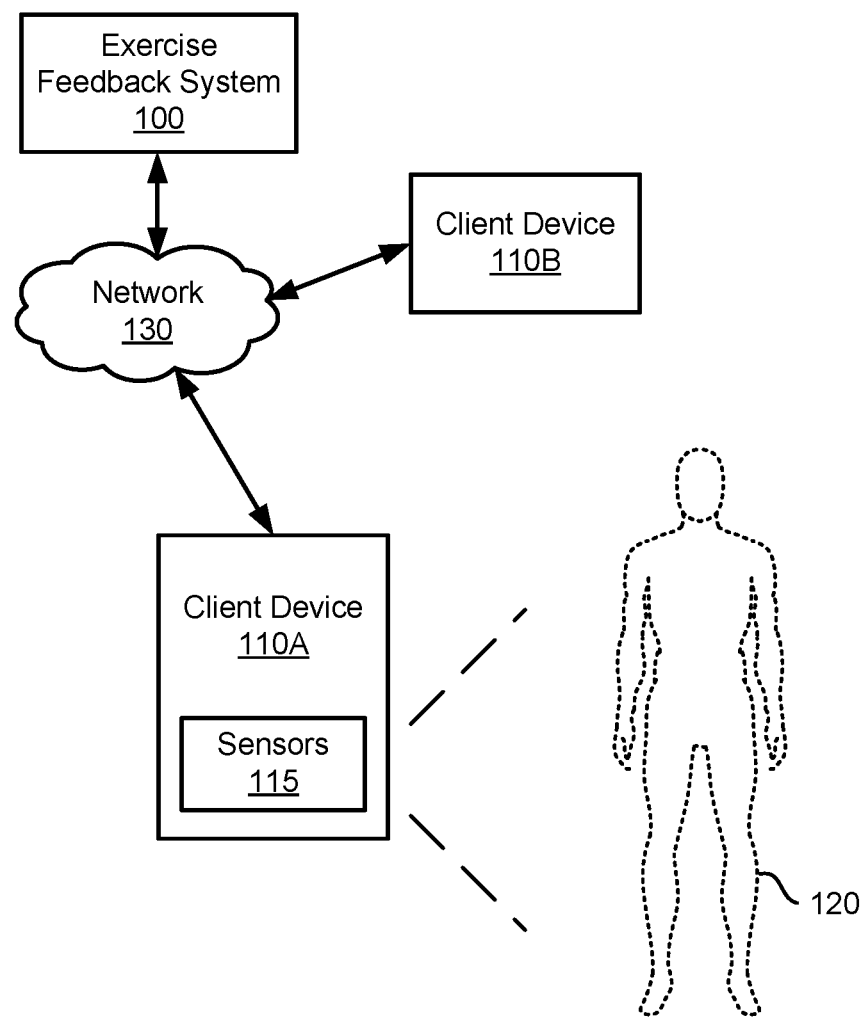
FIG. 1 is a diagram of a system environment for an exercise feedback system according to an embodiment.

FIG. 1 is a diagram of a system environment for an exercise feedback system 100 according to an embodiment. The system environment comprises the exercise feedback system 100 and client devices 110A and 110B (collectively referenced herein as client devices 110 or a client device 110), which are connected to each other via the network 130 (e.g., the Internet or BLUETOOTH®). For clarity, a limited number of client devices 110 are shown. However, other embodiments may include additional client devices 110 of users or providers of the exercise feedback system 100. Furthermore, the system environment may include different or other additional entities.

Users of the exercise feedback system 100 perform exercises, and the exercise feedback system 100 provides feedback to users for performed exercises. For example, the feedback indicates musculoskeletal form of a body 120 of a user to help guide proper form while performing exercises. The feedback may be determined using input from providers of the exercise feedback system 100. For purposes of explanation, this disclosure generally refers to physical therapists as providers. However, the embodiments described herein may be adapted for other types of providers such as athletic trainers, doctors, physicians, coaches, clinicians, nurses, and the like, who are suited to provide input regarding exercise performance or health of users for specific areas or in general.

The client device 110A includes one or more sensors 115 to capture exercise data or other user information of a user before, during, or after performance of an exercise. Sensors 115 may include, e.g., a camera, depth sensor, ultrasound sensor, illumination source, infrared camera, light sensor, proximity sensor, etc. Exercise data may include image data, video data, or other types of exercise-related information. For example, an image indicates musculoskeletal form of the body 120 of the user while performing an exercise. The exercise feedback system 100 provides the image for display on the client device 110B of a provider. The exercise feedback system 100 may generate feedback for the exercise using input (e.g., a classification of musculoskeletal form) received from the provider, and provide the feedback to the client device 110A for display to the user.

In some embodiments, a client device 110 includes an electronic display for presenting images, feedback, or other exercise related information. The electronic display and a camera (or another type of imaging sensor) may be positioned on a same side of the client device 110 such that the user may view feedback displayed on the electronic display while performing an exercise. Particularly, the user may position and orient the client device 110 such that the side including the electronic display and a camera is facing the user. Further, the camera can capture exercise data of the user while the user is performing the exercise (within a field of view of the camera) and viewing the electronic display. In other embodiments, the client device 110 includes a different type of display device (e.g., a projector) for presenting feedback or other media.

Each client device 110 comprises one or more computing devices capable of processing data as well as transmitting and receiving data via the network 130. For example, a client 110 may be a mobile phone, smartphone, augmented reality (AR), virtual reality (VR), or mixed reality device, a desktop computer, a laptop computer, a tablet computing device, an Internet of Things (IoT) device, or any other device having computing and data communication capabilities. A client device 110 may include a processor for manipulating and processing data, and a storage medium for storing data and program instructions associated with various applications.

The exercise feedback system 100 is a computer system configured to store, receive, and transmit data to clients 110 via the network 130. A server may include a singular computing system, such as a single computer, or a network of computing systems, such as a data center or a distributed computing system. The server may receive requests for data from clients 110 and respond by transmitting the requested data to the clients 110. The exercise feedback system 100 is further described below with reference to FIG. 2.

Figure 2:
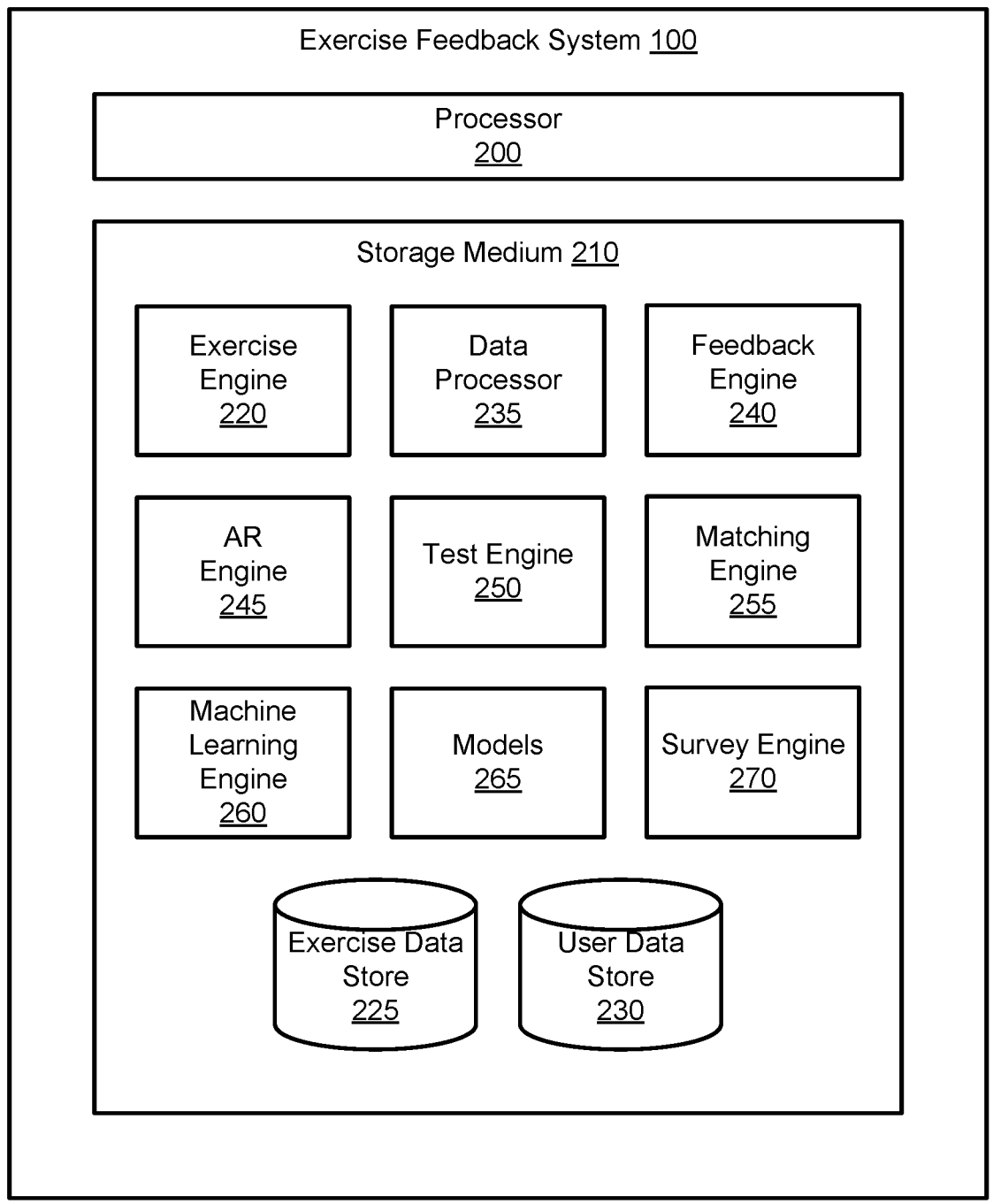
FIG. 2 is block diagram of an exercise feedback system according to an embodiment.

FIG. 2 is block diagram of an exercise feedback system 100 according to an embodiment. The exercise feedback system 100 includes a processor 200 for manipulating and processing data, and a storage medium 210 for storing data and program instructions associated with various modules. The storage medium 210 includes an exercise engine 220, exercise data store 225, user data store 230, data processor 235, feedback engine 240, augmented reality (AR) engine 245, test engine 250, machine learning engine 260, one or more models 265, and survey engine 270. Alternative embodiments may include different or additional modules or omit one or more of the illustrated modules.

The storage medium 210 may include both volatile memory (e.g., random access memory) and non-volatile storage memory such as hard disks, flash memory, and external memory storage devices. In addition to storing program instructions, the storage medium 210 stores various data associated with operation of applications. In one embodiment, the storage medium 210 comprises a non-transitory computer-readable storage medium. Various executable programs are embodied as computer-executable instructions stored to the non-transitory computer-readable storage medium. The instructions, when executed by the processor 200, cause the exercise feedback system 100 to perform the functions attributed to the programs described herein.

The exercise engine 220 provides exercise information to client devices 110. The exercise information may describe exercises to be performed by users. In some embodiments, the exercise information includes one or more types of media (e.g., image, photo, video, text, audio, etc.) indicating a target (e.g., proper or correct) musculoskeletal form or instructions for performing an exercise. The exercise engine 220 can store or retrieve exercise information from the exercise data store 225. For instance, the exercise data store 225 includes a database of multiple types of exercises. Exercises may be organized into different categories, for example, a particular area of the body (e.g., neck, shoulder, elbow, wrist, back, hip, knee, ankle, whole body) or level of difficulty.

In some embodiments, exercise information includes exercise workouts, e.g., to be completed in one session. An exercise workout includes one or more exercise sets, and an exercise set includes a number of repetitions of an exercise. For exercises involving weights (e.g., a barbell or dumbbell), the exercise set may be associated with an amount of weight for the set. In addition, the exercise workout may have an expected duration of time (required to complete the exercises) and one or more goals. Goals may be aimed at improving flexibility, mobility, stamina, or strength of at least one particular area of the body, overall health, or for performing under certain conditions (e.g., indoors at an office vs. at a gym with more equipment). Exercise workouts may indicate certain equipment required for one or more of the exercise sets, e.g., a towel, chair, table, step, band, foam roller, bench, wall, etc.

The exercise engine 220 manages user profiles of users and providers of the exercise feedback system 100. The exercise engine 220 may store or retrieve user information from the user data store 230. User information may include, for example, demographic data, geographical location, media (e.g., an uploaded photo of a user), adherence in completing exercises, preferences, or other relevant information. The exercise engine 220 may manage associations between users and providers. For instance, a user may have one or more providers (e.g., a general physical trainer and a back pain specialist), and a provider may have one or more users as patients. The exercise engine 220 may track exercises previously performed by a user, currently being performed by a user, or recommended for a user by the exercise feedback system 100. In some embodiments, the exercise engine 220 determines an adherence of a user by determining a timestamp of the most recently performed exercise by the user. As other examples, the exercise engine 220 can determine adherence based on a percentage of scheduled exercise workouts that user actually completed, or a percentage of exercises, sets, or repetitions of a certain workout completed by the user. In some embodiments, the exercise engine 220 determines adherence by determining whether a user performed exercises using proper musculoskeletal form or using a target amount of weight (e.g., for strength training exercises).

The data processor 235 processes sensor data received from client devices 110. The data processor 235 may use image or video processing techniques known to one skilled in the art to analyze media captured by client devices 110. In some embodiments, the data processor 235 uses object detection or edge detection algorithms to determine position or orientation of a user as shown in an image or frame of a video. For example, the data processor 235 determines an angle of a joint or portion of the body of a user by detecting orientation of two adjacent segments of the body (e.g., upper and lower arms or legs).

The feedback engine 240 provides feedback to client devices 110. The feedback may indicate whether a user is performing or performed an exercise with proper musculoskeletal form. The feedback may be a Boolean (e.g., proper or improper) or a numeric value such as a score or a metric (e.g., an angle of a joint of the body, or a rating of how closely a user matches the proper form). In various embodiments, feedback may also include comments, classifications, or other text describing performance of an exercise (e.g., "extend arm" or "straighten back"). The feedback may indicate a target, e.g., proper, musculoskeletal form. For instance, feedback indicates that the knee should be bent at (or approximately) a 90 degree angle for a portion of a given exercise. In some embodiments, the feedback describes trends (e.g., generated by the survey engine 270 further described below) in scores or metrics for historical musculoskeletal forms of a user while performing exercises. A trend may indicate changes corresponding to an improvements or decline in proper musculoskeletal form. Trends may also be associated with other types of metrics or information such as number of exercises performed, adherence to an exercise program, interactions with providers, weights for strength-related exercises, etc.

The AR engine 245 provides augmented reality (AR) graphics to client devices 110 to guide exercises. The AR engine 245 may overlay an AR graphics on a video feed captured by a sensor 115 of a client device 110. In some embodiments, the AR engine 245 personalizes an AR graphic using user information. For instance, the exercise feedback system 100 determines an image of a user indicative of proper musculoskeletal form (e.g., according to input from a provider or a target musculoskeletal form for reference), and the AR engine 245 generates an AR graphic using at least the image. In comparison to an AR graphic based on a generic avatar, a personalized AR graphic may provide a more engaging user experience by helping the user visualize the proper musculoskeletal form. In some embodiments, the AR engine 245 generates a visual representation of the user in 3D using depth information of video data or other data captured by a depth imaging sensor of a client device 110. The client device 110 may provide the visual representation and AR graphic for display in 3D.

The test engine 250 may perform one or more types of tests using information from exercises performed by users of the exercise feedback system 100. In some embodiments, the test engine 250 performs AB tests to evaluate or compare users. For example, the test engine 250 receives a first and second set of images captured by a client devices 110 of a first and second group of users, respectively. The first group is a test group of users who performed a given exercise during a period of time, while the second group is a control group of users who did not perform the given exercise during the same period of time. The test engine 250 may provide a notification to the control group including instructions to not perform the given exercise, or the test engine 250 may determine to not provide a notification to the control group regarding the given exercise (thus assuming that the control group will not perform the given exercise at least during a period of time). The test engine 250 may determine groups of users from a population of users of the exercise feedback system 100 using demographic information or physiological information of the users. For instance, to control other variables in an A/B test, the test engine 250 selects users for the test and control groups that have the same or similar attributes, e.g., age range, ethnicity, or geographical area. In addition, the test engine 250 may select a number of users to form a statistically significant sample size. In some embodiments, test engine 250 performs A/B tests for clinical trials to evaluate musculoskeletal exercises, exercise performance of users, or feedback from providers.

Following in the above example, the test engine 250 receives a first and second set of classifications of musculoskeletal form for the first and second group, respectively, e.g., determined by the feedback engine 240. The test engine 250 compares the first and second sets of classifications to determine potential correlations based on whether or not the users performed the exercises during the period of time. For instance, the test engine 250 may determine that the test group of users improved one or more health metrics (e.g., pain levels, sleep quality, mobility, strength, etc.), while the control group did not improve those metrics. In some embodiments, the test engine 250 uses a reference of known proper musculoskeletal form (e.g., a "gold standard") to evaluate performance of users. The reference may indicate a target angle between a first segment and a second segment of the body of a user while performing at least of a portion of an exercise. As examples, the reference may indicate a target angle of 90 degrees between an arm and forearm, or that the neck and back should be parallel during a stage of an exercise.

In some embodiments, the test engine 250 generates provider scores for providers by comparing classifications provided by the providers. For example, the test engine 250 receives a first and second set of classifications from a first and second set of providers, respectively. The classifications may include feedback for a same group of users or type of exercise. The test engine 250 generates provider scores indicating whether the first or second set of providers provided more accurate classifications, e.g., by comparing the first and second set of classifications. A provider score may indicate one or more different metrics of the classifications. For instance, the metric is a percentage, rating, or other numerical value that indicates a level of quality or reliability of the corresponding provider's feedback. The test engine 250 may use a known set of proper classifications or a target musculoskeletal form as a reference for comparison. In an embodiment, the test engine 250 may determine average classifications across an aggregate set of provider classifications and use the average in comparisons to identify outlier classifications (e.g., which are low quality or unreliable). In other embodiments, the test engine 250 can generate provider scores for providers without a comparison between providers.

In some embodiments, the test engine 250 provides functional tests to users, e.g., to determine a certain range of motion or physical condition of a user. As examples, the test engine 250 provides instructions for a user to perform a squat exercise to evaluate the user's balance, or to perform an arm exercise to evaluate the user's upper body flexibility of a certain joint or muscle. The test engine 250 may compare musculoskeletal form indicated by an image or photo of the user performing a functional test against a target musculoskeletal form for the functional test to determine a test metric. The test metric indicates a level of the user's performance for the functional test. For example, the test metric indicates an angle to which the user is able to bend the user's legs at the knee during the squat exercise, or whether the user's back remains approximately straight while performing the squat.

The matching engine 255 determines recommendations for users and providers of the exercise feedback system 100. The matching engine 255 may recommend one or more candidate providers to a user responsive to determining that the candidate providers are likely to be a good match for the user. For example, the matching engine 255 receives user information for a new user who joins the exercise feedback system 100, where the user information describes at least one preference of the user. The preference may be associated with an attribute of a provider, e.g., the user wants a physical therapist having a particular gender, level of experience, area of expertise, language spoken, style of practice, etc. In some embodiments, the matching engine 255 determines candidate providers using provider scores of the providers generated by the test engine 250. For instance, the matching engine 255 filters out candidate providers having provider scores less than a threshold value. The matching engine 255 may send a notification to a client device 110 of a provider that requests the provider to reject or accept a match to a certain user.

The machine learning engine 260 trains one or more models 265 for providing feedback to providers or users of the exercise feedback system 100. In an embodiment, the machine learning engine 260 trains a model 265 to score users based on exercise information, user information, other types of training data, or some combination thereof. The model 265 may take as input images of a user while performing exercises and generates a score, which may indicate a level of urgency to which the user needs feedback or attention from a provider. As an example, responsive to the model determining that the user's musculoskeletal form for an exercise is improper or may likely cause the user to become more vulnerable to injury or discomfort, the model determines a higher level of urgency for the user. As a different example, responsive to the model determining that the user's musculoskeletal form is proper, the model determines a lower level of urgency because the user has a lower risk of injury or encountering other types of issues with exercising.

In some embodiments, the model 265 generates scores using multiple signals describing users, which may be determined by other components of the exercise feedback system 100 or sources external to the exercise feedback system 100. The signals may include a level of difficulty of exercises, level of pain during or after performance of exercises, exercise adherence, etc. Furthermore, the model 265 may determine sub-scores for different signals and generate the score by determining a weighted average of the sub-scores. The model 265 may assign greater weights for certain signals that are determined to be more predictive indicators of a user's need for feedback or intervention from a provider.

The survey engine 270 conducts surveys to collect information from users or providers of the exercise feedback system 100. In some embodiments, the survey engine 270 provides survey questions for display to client devices 110 periodically over a period of time, e.g., instead of providing all questions for a survey at once. Additionally, the survey engine 270 may determine trends by aggregating response to survey questions over the period of time. For example, the survey engine 270 determines a moving average of a user-reported metric for exercises. The survey engine 270 may receive user-reported metrics of a given user in response to providing multiple instances of a same (or similar) question to a client device 110 of the given user. For instance, a question for the given user asks, "How much pain do you feel after completing the exercise?" The metric may be a numerical value, a category (e.g., none, low, medium, or high level of pain), Boolean, or another type of value.

The moving average may indicate trends in a user's perceived level of pain, level of difficulty, mobility, or strength while performing exercises or on a regular daily basis. Further, the survey engine 270 can use moving averages to determine long-term changes or patterns in user performance or condition, for example, an increase in mobility or decrease in level of pain or exercise difficulty over several weeks or months, by smoothing out short-term variations on a day-to-day or exercise workout-to-workout basis. In some embodiments, the survey engine 270 provides information describing the trends for presentation on a client device 110 of a user. Additionally, the survey engine 270 may determine one or more images corresponding to the user and a trend. For instance, the survey engine 270 provides a graphic for display indicating a gradual increase in the user's reported levels of pain, and the graphic includes images of the user performing certain exercises for which the user reported relatively greater levels of pain.

In some embodiments, the survey engine 270 provides a moving average of a metric as input or training data to one of the models 265. Thus, a model 265 may learn to develop a risk profile of a user and use the risk profile to determine scores indicating levels of urgency for feedback. For instance, the model 265 determines that a user who has reported chronic levels of pain above a threshold, or a history of physical injuries, is likely to require more urgent intervention from a provider.

The survey engine 270 may customize delivery of survey questions according to when a user is likely to respond or interact with the exercise feedback system 100. As an example, the survey engine 270 determines a timestamp when a response to a questions is received from a client device 110 of a user. The survey engine 270 provides another question to the same client device 110 (or another client device of the same user) at a time determined using the timestamp. For instance, the survey engine 270 determines a certain time of day or the week or month at which the user typically exercises or reviews feedback or other information using the exercise feedback system 100.

Figure 3:
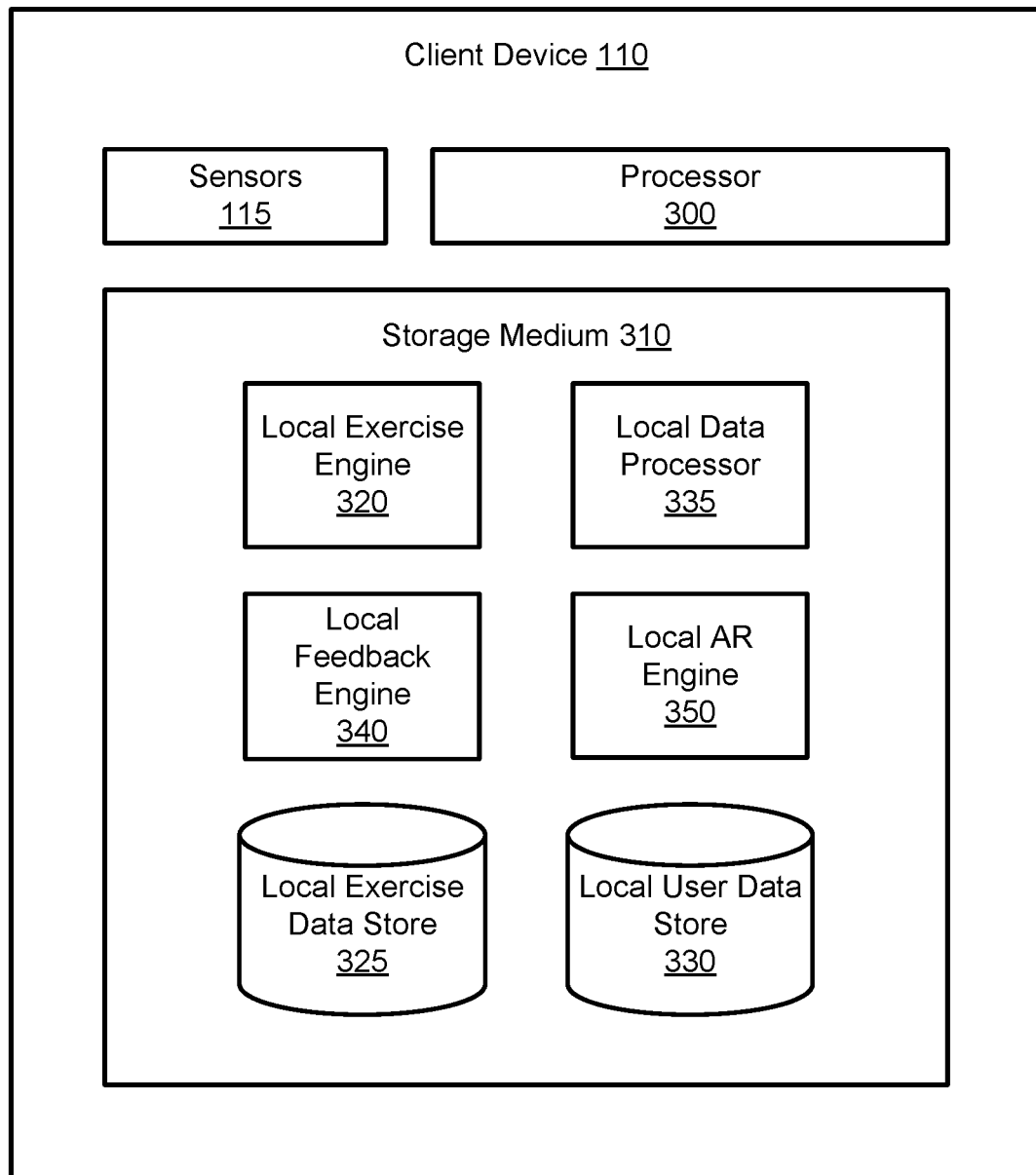
FIG. 3 is block diagram of a client device according to an embodiment.

FIG. 3 is block diagram of a client device 110 according to an embodiment. The client device 110 includes one or more sensors 115, a processor 300 for manipulating and processing data, and a storage medium 310 for storing data and program instructions associated with various modules. The storage medium 310 includes a local exercise engine 320, local exercise data store 325, local user data store 330, local data processor 335, local feedback engine 340, and local augmented reality (AR) engine 350. Alternative embodiments may include different or additional modules or omit one or more of the illustrated modules. The components of the storage medium 310 are substantively the same as the corresponding components of the exercise feedback system 100 shown in FIG. 2. Thus, the client device 110 may perform at least some functionality of the exercise feedback system 100 locally, e.g., without necessarily requiring a network connection.

Example User Interfaces

Figure 4:
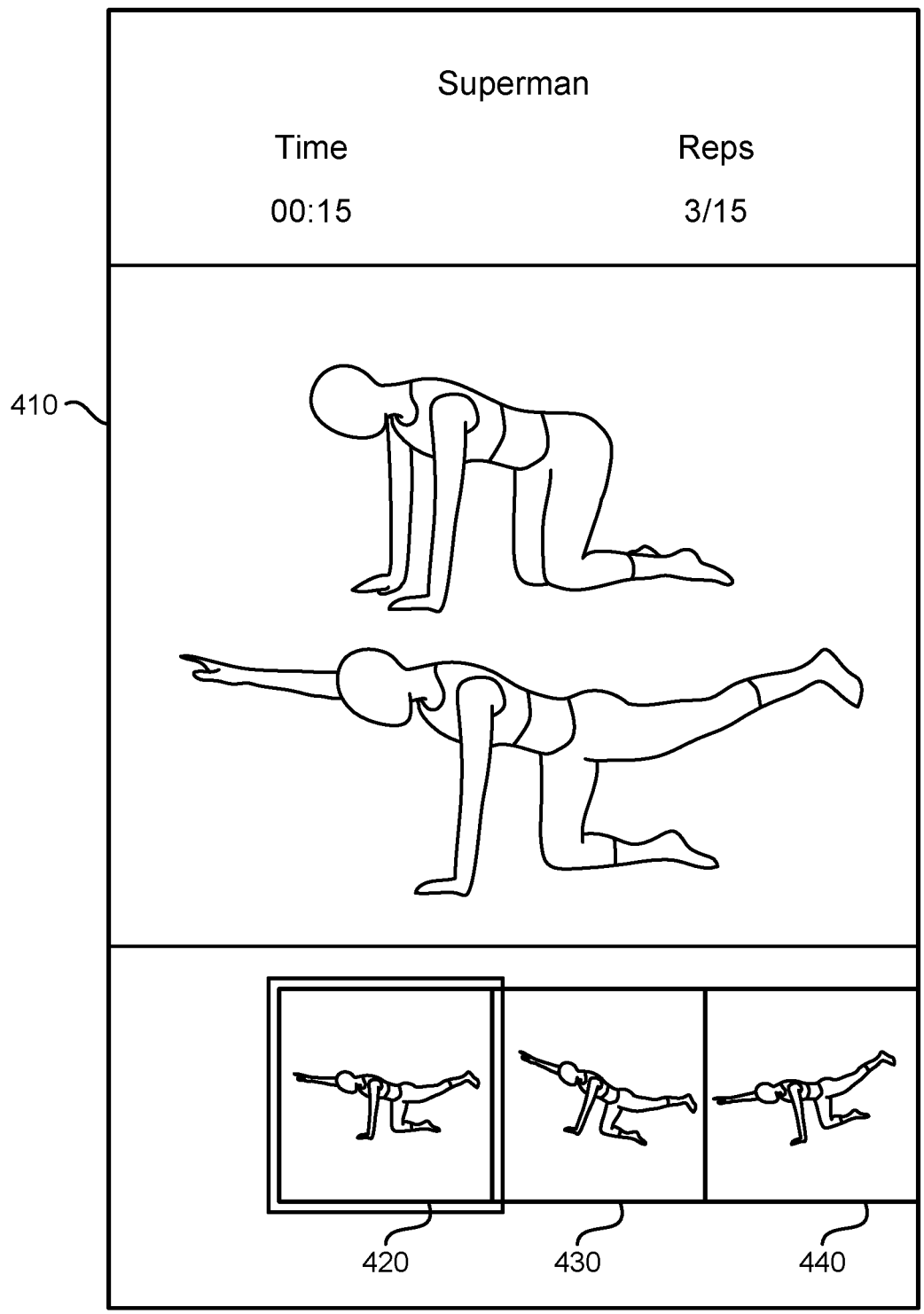
FIG. 4 is a diagram of an example user interface layout for a user of the exercise feedback system according to an embodiment.

FIG. 4 is a diagram of an example user interface layout 400 for a user of the exercise feedback system 100 according to an embodiment. To present a target musculoskeletal form for a kneeling superman exercise (e.g., for training back strength and stability), the exercise engine 220 may generate the user interface layout 400, which includes images 410 of an avatar in two positions. The top avatar shows a starting position and the bottom avatar shows an extended position for the exercise. In addition, the user interface layout 400 also indicates a running timer and repetitions (e.g., repetitions completed or total in a set). The user interface layout 400 includes a set of images 420, 430, and 440, e.g., photos captured by a camera sensor 115 of a user's client device 110. A repetition of the exercise may correspond to one or more of the images; e.g., images 420, 430, and 440 show the user's musculoskeletal form while performing the first, second, and third repetitions, respectively, of a set for the exercise. In some embodiments, the images may be animated images or videos, or include 3D information.

The feedback engine 240 may receive a selection of one or more of the images and provide the selected images to a different client device 110 of a provider of the user. For instance, as illustrated by the graphical outline in FIG. 4, the feedback engine 240 determines that the user selected image 420, e.g., because the user believes that image 420 shows the user's best musculoskeletal form among the set of images, in terms of matching the target musculoskeletal form. The feedback engine 240 may also provide a duration of time that the user took to complete one or more repetitions of the exercise. In some embodiments, the feedback engine 240 provides a breakdown of the time required per repetition, so that a provider can determine whether the user struggled when completing a specific repetition.

Figure 5:
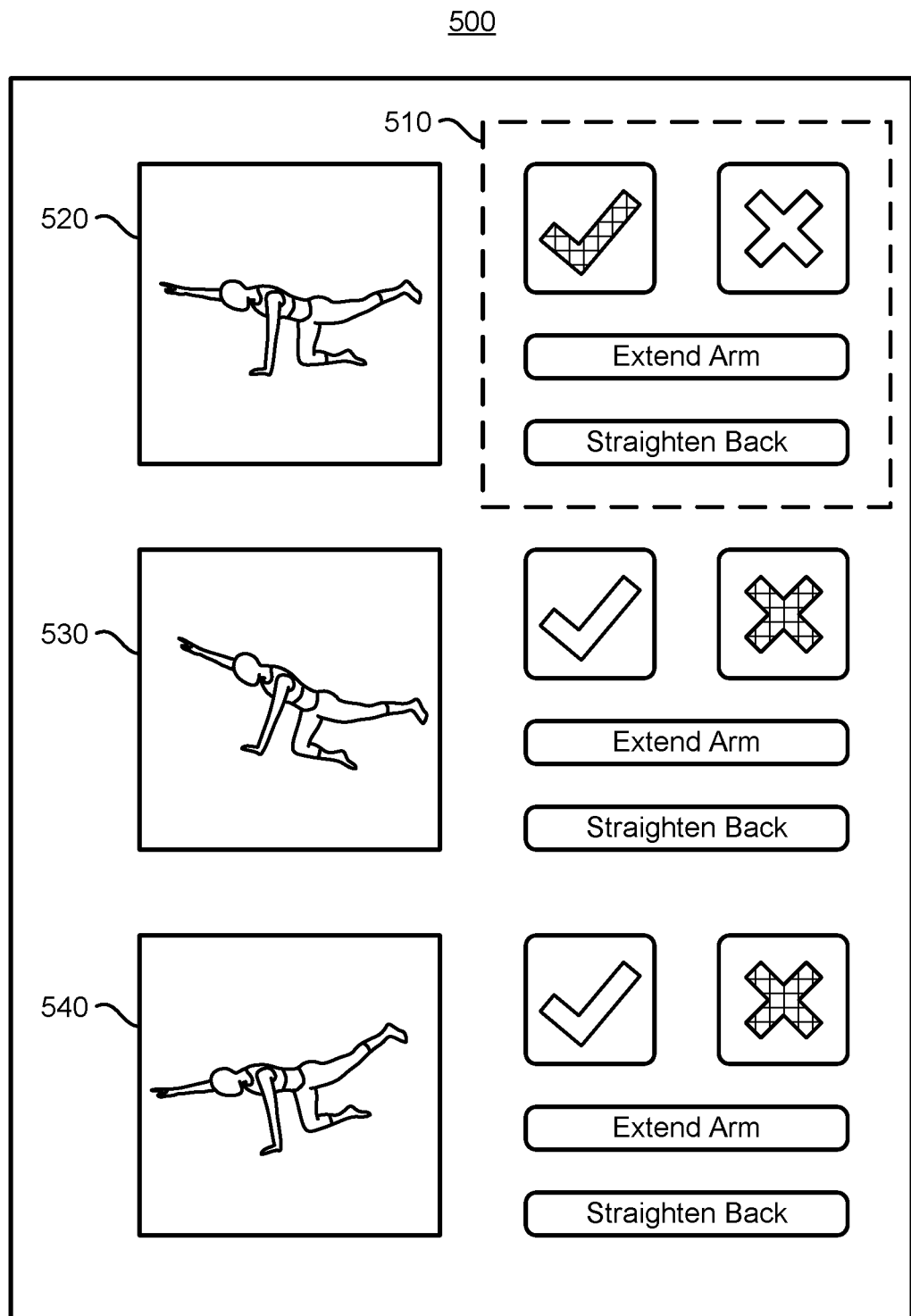
FIG. 5 is a diagram of an example user interface layout for a provider of the exercise feedback system according to an embodiment.

FIG. 5 is a diagram of an example user interface layout 500 for a provider of the exercise feedback system according to an embodiment. The exercise engine 220 may generate the user interface layout 500 for a provider to review and provide feedback regarding exercise performance of users. In the example shown in FIG. 5, the user interface layout 500 includes images (e.g., or photos or videos) 520, 530, and 540 of a user performing the kneeling superman exercise described above with reference to FIG. 4. For each of the images, the user interface layout 500 also includes user inputs for a provider to select. Specifically, the provider may use the user inputs 510 to provide feedback on musculoskeletal form of the user as depicted in image 520. In some embodiments, the user inputs 510 may include buttons representing various types of feedback, for example, a Boolean value (e.g., proper form as indicated by a check mark or improper form as indicated by the cross mark) or a certain type of advice (e.g., represented by strings or text such as "extend arm" or "straighten back").

Figure 6:
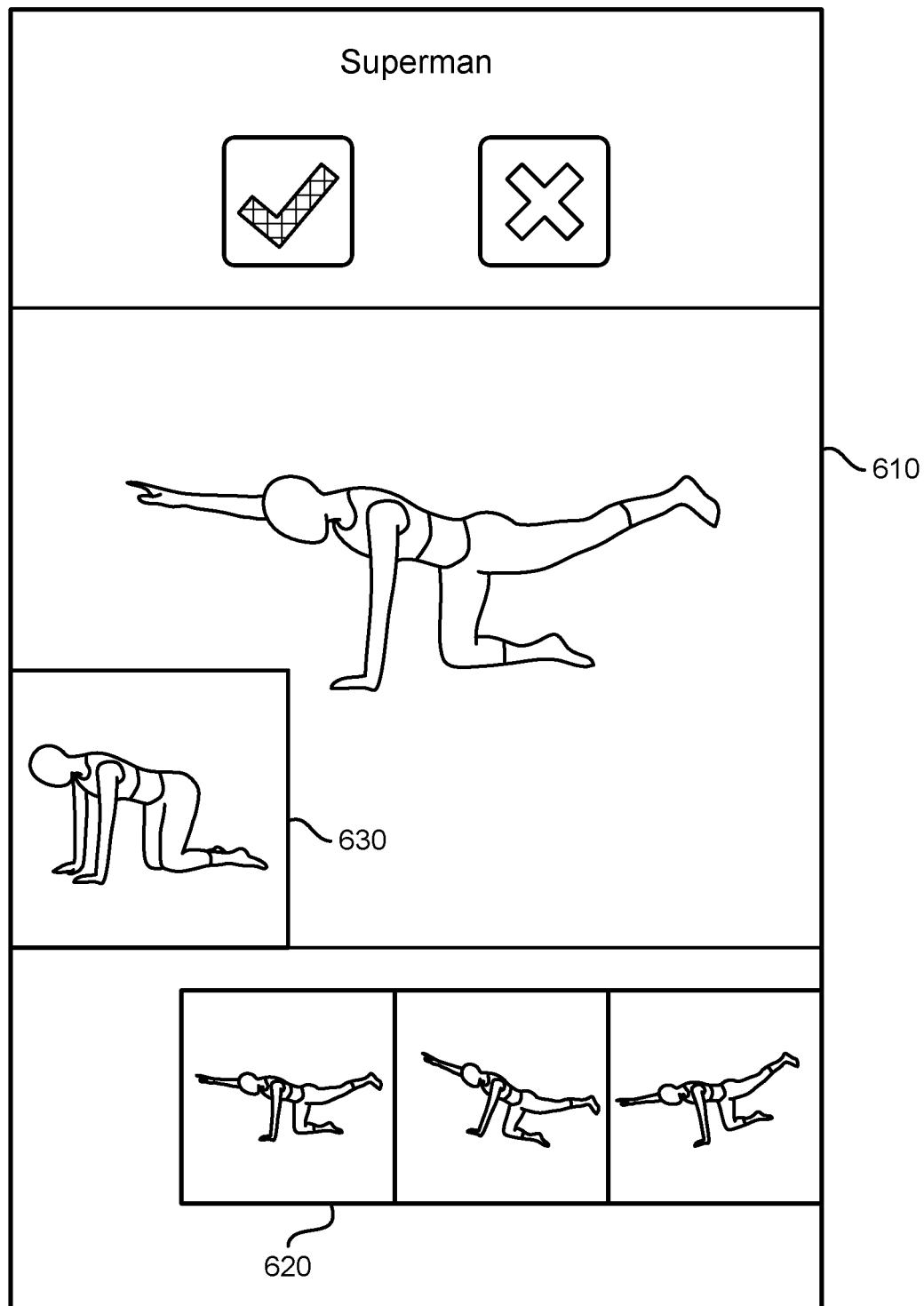
FIG. 6 is a diagram of another example user interface layout for a provider of the exercise feedback system according to an embodiment.

FIG. 6 is a diagram of another example user interface layout 600 for a provider of the exercise feedback system 100 according to an embodiment. The exercise engine 220 may generate the user interface layout 600 for a provider to review and provide feedback regarding exercise performance of users. Similar to the user interface layout 400 for a user, the example user interface layout 600 includes a set of images 620 indicating musculoskeletal form of a user performing an exercise. The user interface layout 600 may include an enlarged view 610 of a selected image of the set of images 620. Additionally, the user interface layout 600 may include a real time video feed 630 of the user such that the provider can determine and provide feedback via the exercise feedback system 100 while the user is performing exercises.

Figure 7:
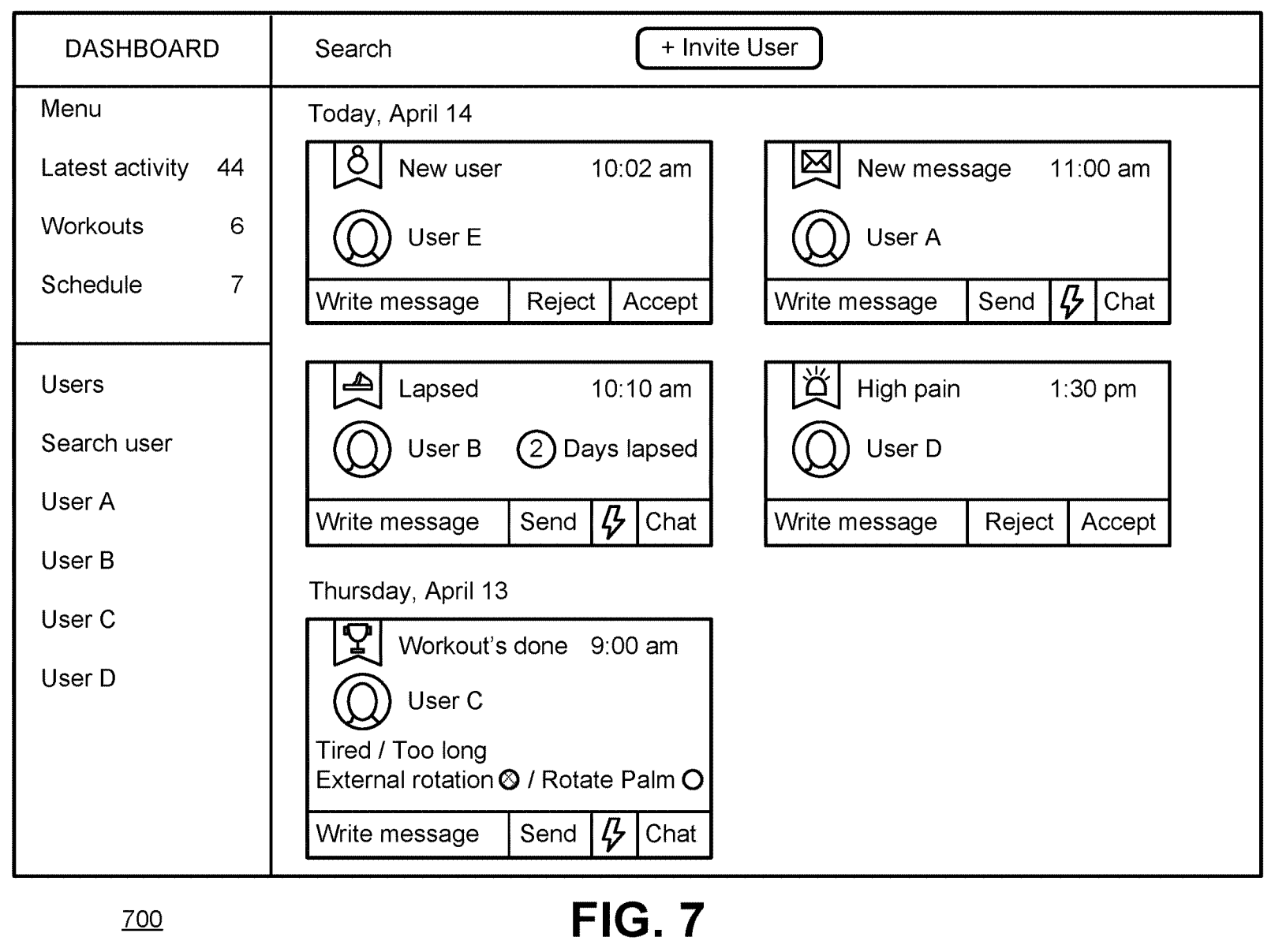

FIG. 7 is a diagram of an example user interface layout 700 including aggregate information for multiple users of the exercise feedback system according to an embodiment. The exercise engine 220 may generate the user interface layout 700 as a dashboard for a provider such as a physical trainer. The user interface layout 700 includes a central feed including content items describing users associated (e.g., having a client relationship as a patient) with the physical trainer, where each content item may have a timestamp and indicate a certain type of user status or information. The exercise engine 220 may order the content items at least partly based on chronological order by date and time. In the example shown in FIG. 7, the central feed includes at least five content items over the period of April 13-14. A content item at 10:02 am on April 14 indicates that a new "User E" has joined the exercise feedback system 100. The content item includes a reject and accept button for the physical trainer to select whether to set up a client relationship with the new user, e.g., who is in search of exercise feedback or training. Content items may also include functionality for a physical trainer to send a message (e.g., direct/private or group/public) to users or receive messages from other users.

Following in the same example user interface layout 700, the central feed also includes a content item at 10:10 am on April 14 indicating that "User B" has lapsed for two days. Accordingly, the physical trainer may be alerted of the lapse and follow-up with "User B" regarding adherence to exercise workouts. In addition, the central feed includes a content item at 11:00 am on April 14 indicating that a new message has been received from "User A." Furthermore, the central feed includes a content item at 1:30 pm on April 14 indicating that "User D" reported high levels of pain for an exercise. For April 13, the central feed includes a content item at 9:00 am indicating that "User C" completed a workout. The content item also includes feedback from the "User C," which indicate that the user is "tired" and thought that the exercise workout was "too long." The content item can also indicate one or more types of exercises performed by or scheduled for the user.

Figure 8A:
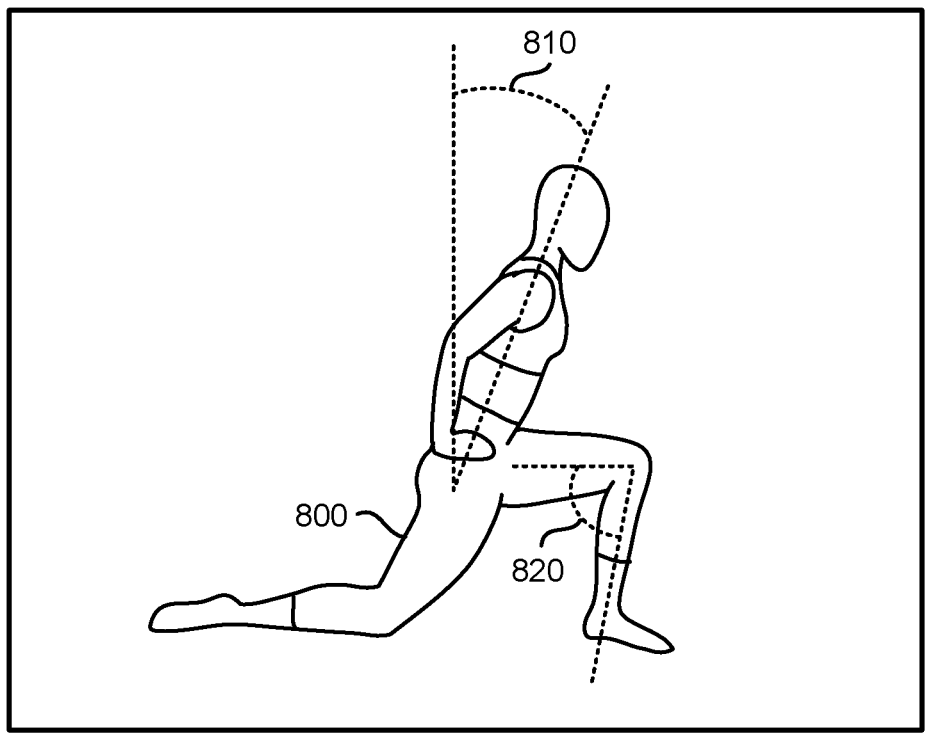
FIG. 8A is a diagram of an example visual representation of a user of the exercise feedback system according to an embodiment.

FIG. 8A is a diagram of an example visual representation 800 of a user of the exercise feedback system 100 according to an embodiment. The visual representation 800 may be part of a video feed or video data captured by a camera of client device 110 of the user while performing or preparing to perform an exercise. The exercise engine 220 may provide instructions for display on the device 110 to indicate a target orientation of the client device 110 for capturing the video data, e.g., landscape or portrait orientation based on the type of the exercise. In the example of FIGS. 8A-D, the user is performing a lunge exercise. The dotted lines superimposed on the visual representation 800 indicate that the user's back is positioned at an angle 810 relative to the vertical. In addition, the dotted lines indicate that the user's lower leg is at another angle 820 relative to the user's thigh. Note that the dotted lines are used for explanation to illustrate angles between different segments of the body of the user, and not necessarily displayed in a user interface to be visible to the user. The data processor 235 may analyze the video data to determine the angles 810 and 820 during the exercise.

Figure 8B:
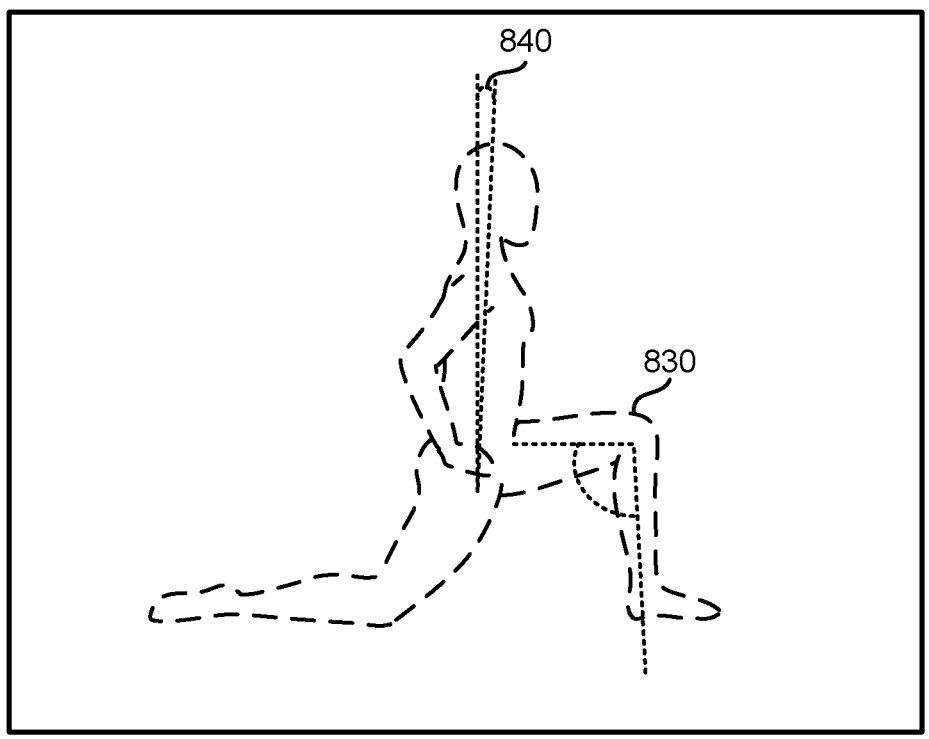
FIG. 8B is a diagram of an example augmented reality graphic according to an embodiment.

FIG. 8B is a diagram of an example augmented reality graphic 830 according to an embodiment. The AR graphic 830 indicates a target musculoskeletal form for the lunge exercise corresponding to the example described with reference to FIG. 8A. As shown by the example dotted lines in FIG. 8B, the target musculoskeletal form indicates that the back of a user should be aligned approximately to the vertical within a threshold angle 840 of error, e.g., 0 to 10 degrees. Further, the target musculoskeletal form indicates the lower leg should be approximately at a 90 degree angle relative to the thigh.

Figure 8C:
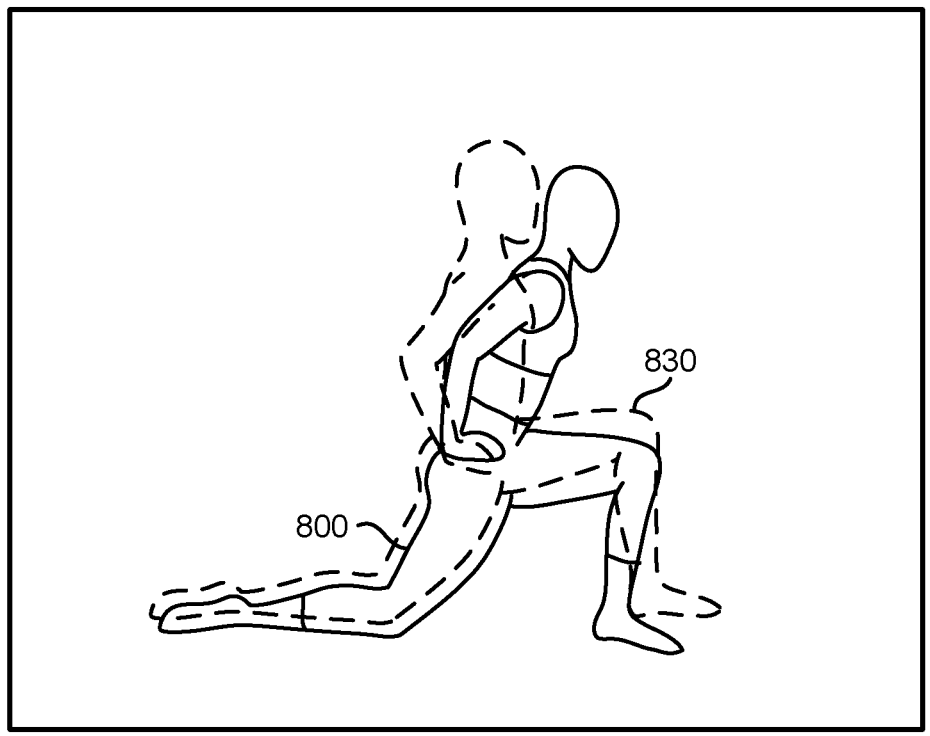
FIG. 8C is a diagram of an example composite view of the augmented reality graphic shown in FIG. 8B overlaid on the visual representation of the user shown in FIG. 8A according to an embodiment.

FIG. 8C is a diagram of an example composite view of the augmented reality graphic 830 shown in FIG. 8B overlaid on the visual representation 800 of the user shown in FIG. 8A according to an embodiment. The AR graphic may be an avatar representing a target proper musculoskeletal form for a given exercise. The AR engine 245 may generate the composite view including the AR graphic 830 that is at least partially transparent such that a user can view both the AR graphic 830 and the visual representation 800 simultaneously, e.g., being displayed on a user interface of a client device 110. Thus, the user may perceive the AR graphic as a "projected guiderail" in an AR environment, and the user can use the AR graphic 830 as a visual guide to determine the target musculoskeletal form for a starting position of the lunge exercise. As the body of the user moves, the AR engine 245 may update the visual representation 800 of the composite view in real time to reflect the latest position or movement of the body. The AR engine 245 may store AR graphics in the exercise data store 225 or retrieve previously generated AR graphics from the exercise data store 225.

Figure 8D:
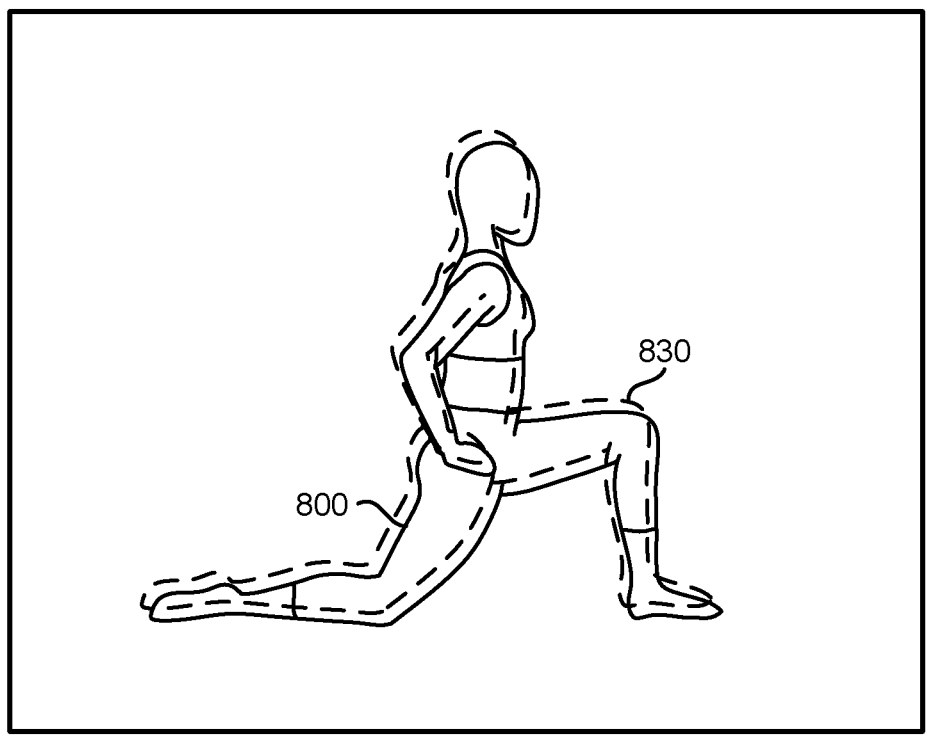
FIG. 8D is a diagram of another example composite view according to an embodiment.

FIG. 8D is a diagram of another example composite view according to an embodiment. In comparison to the composite view shown in FIG. 8C, the composite view shown in FIG. 8D includes a visual representation 800 of the user that more closely matches the AR graphic 830. In some embodiments, the data processor 235 determines a level of similarity between the visual representation 800 and the AR graphic 830 based on the captured positions or orientations or certain segments of the user's body, or one or more angles between particular segments or portions of the body. The AR engine 245 may determine that the visual representation 800 matches the AR graphic 830 responsive to the data processor 235 determining that the level of similarity satisfies a criteria. For example, the data processor 235 compares differences between one or more angles of body segments of user in the visual representation 800 (described above with respect to FIG. 8A) and corresponding target angles indicated by the target musculoskeletal form of the lunge (described above with respect to FIG. 8B) against a threshold value (e.g., an acceptable angle of error). Responsive to determining that the differences in one or more angles are less than the threshold value, the data processor 235 determines that the level of similarity satisfies the criteria. In some embodiments, the threshold value may vary between different target angles of the target musculoskeletal form. In other embodiments, the data processor 235 may compare the overlapping or non-overlapping areas of the visual representation 800 and the AR graphic 830 to determine whether the criteria is satisfied.

In an example use case, the exercise engine 220 determines to start an exercise program responsive to the data processor 235 determining that the level of similarity satisfies the criteria. As another use case, the exercise engine 220 may determine to capture an image or photo or start recording video data of the user responsive to the criteria being satisfied. In an embodiment, responsive to determining that the level of similarity does not satisfy the criteria (e.g., within a predetermined timeout), the exercise engine 220 may provide guidance indicative of the target musculoskeletal form for the exercise. For instance, the guidance indicates that the user need to straighten the back of the user's body achieve the target musculoskeletal form.

Example Process Flows

Figure 9:
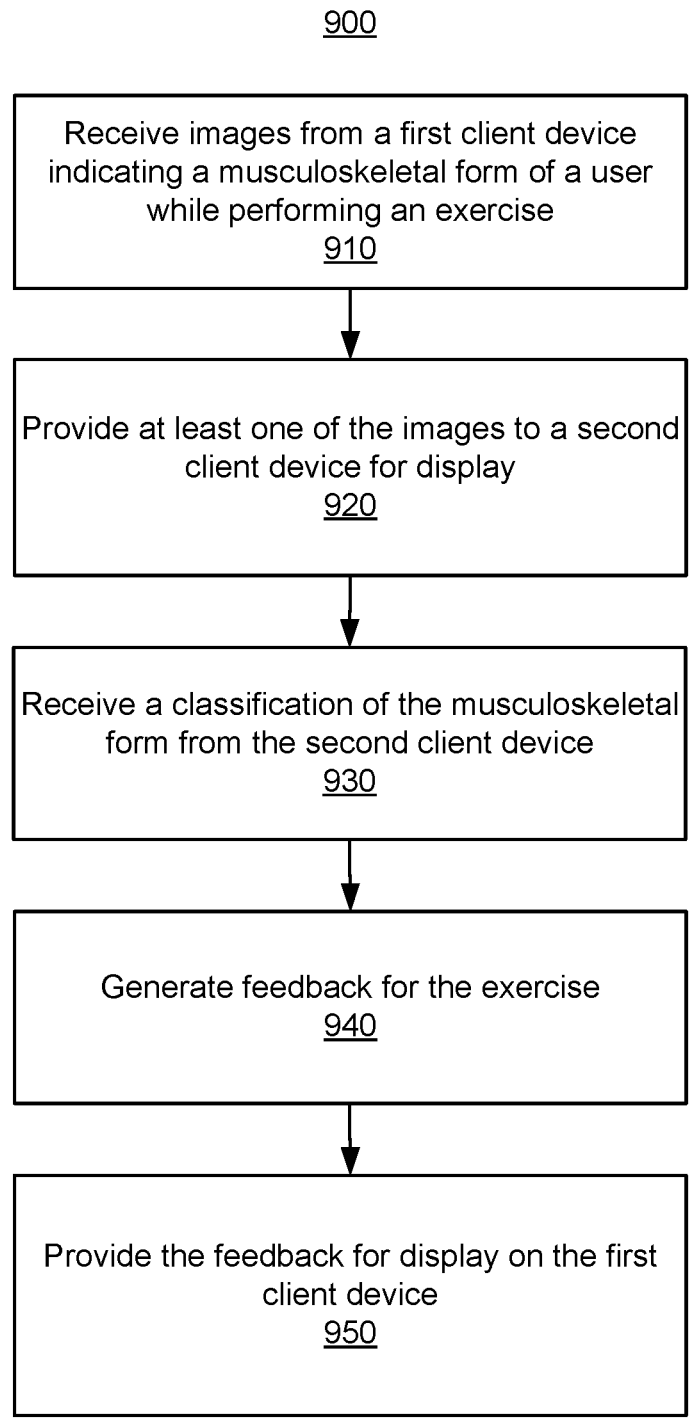
FIG. 9 is a flowchart illustrating a process for providing feedback for musculoskeletal exercises according to one embodiment.

FIG. 9 is a flowchart illustrating a process 900 for providing feedback for musculoskeletal exercises according to one embodiment. In some embodiments, the process 900 is performed by the exercise feedback system 100 within the system environment in FIG. 1. The process 900 may include different or additional steps than those described in conjunction with FIG. 9 in some embodiments or perform steps in different orders than the order described in conjunction with FIG. 9.

In an embodiment, the exercise feedback system 100 receives 910 a set of one or more images (e.g., or photos or videos) from a first client device 110 of a user. The set of images are captured by a camera of the first client device 110, and the set of images indicate musculoskeletal form of the user while performing an exercise. The exercise feedback system 100 provides 920 at least one image of the set of images for display to a second client device 110, e.g., of a provider of the user. The exercise feedback system 100 receives 930 from the second client device 110 a classification of the musculoskeletal form (e.g., proper or improper) of the user responsive to providing the image.

The exercise feedback system 100 generates 940 feedback for the exercise using at least the classification. The feedback may indicate the classification or provide information about trends based on aggregated exercise data or classifications. In some use cases, the feedback includes relevant media such as images, photos, or videos (e.g., to illustrate proper or improper form for comparison). The exercise feedback system 100 provides 950 the feedback for display to the user on the first client device 110. The provider and user may be in different locations (e.g., at home, gym, office, park, etc.). Thus, the exercise feedback system 100 may use the method 900 to provide customized exercise feedback to users even when their providers are not in the same physical space. Additionally, providers may track and provide feedback to users in real time during an exercise workout, or after users have completed an exercise workout.

In an embodiment, responsive to receiving the classification from the second client device 110, the exercise feedback system 100 labels one of the provided images. The label may indicate whether the image shows the user using proper or improper musculoskeletal form for the exercise. As a different example, the label may indicate other types of feedback from a provider such as a recommendation to modify musculoskeletal form or an identification of an area of weakness that needs improvement. The exercise feedback system 100 may provide the feedback by displaying the labeled image on the first client device 110.

Figure 10:
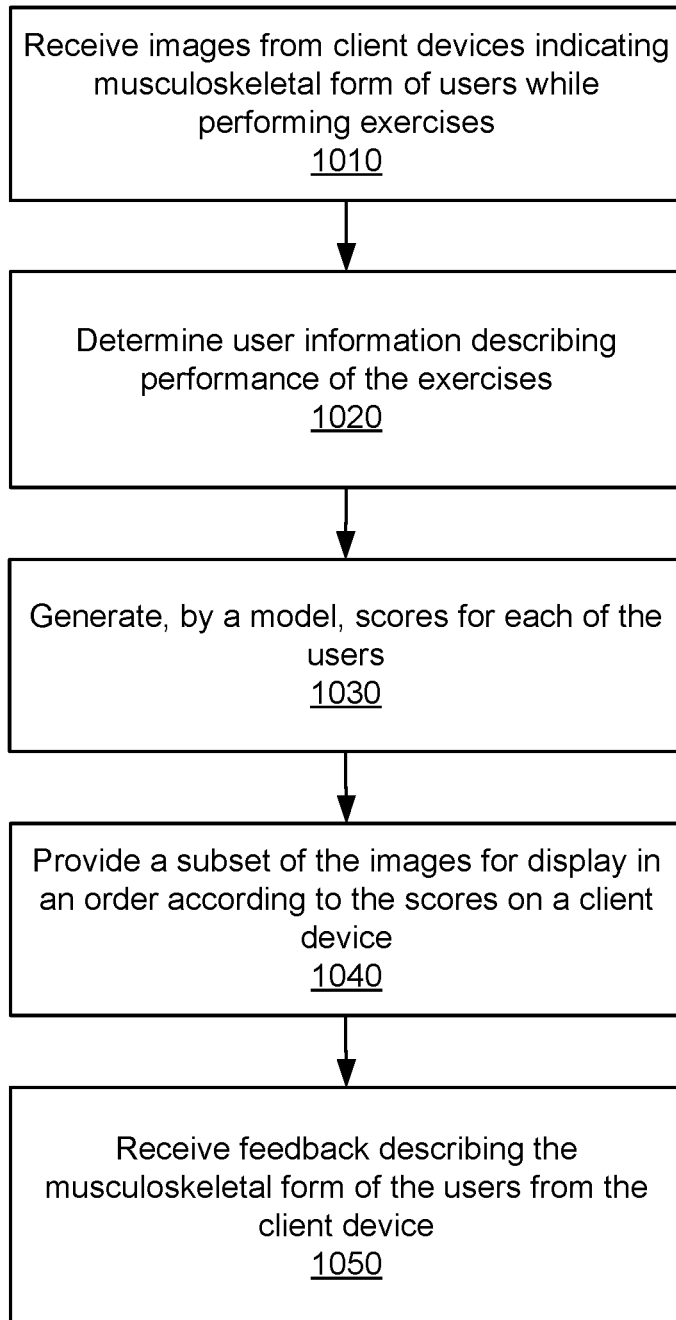
FIG. 10 is a flowchart illustrating a process for providing musculoskeletal form information of users performing exercises according to one embodiment.

FIG. 10 is a flowchart illustrating a process 1000 for providing musculoskeletal form information of users performing exercises according to one embodiment. In some embodiments, the process 1000 is performed by the exercise feedback system 100 within the system environment in FIG. 1. The process 1000 may include different or additional steps than those described in conjunction with FIG. 10 in some embodiments or perform steps in different orders than the order described in conjunction with FIG. 10.

In an embodiment, the exercise feedback system 100 receives 1010 images from client devices 110 of users of the exercise feedback system 100. The images indicate musculoskeletal form of the users while performing exercises. The exercise feedback system 100 determines 1020 user information describing performance of the exercises by the users. The exercise feedback system 100 generates 1030, by a model 265 receiving the images and the user information as input, a score for each of the users. In some use cases, a physical trainer associated with the users uses a client device 110 to provide the feedback describing the musculoskeletal form of the users to the exercise feedback system 100. Each score may indicate, for the corresponding user, a level of urgency for attention or feedback from the physical trainer.

The exercise feedback system 100 provides 1040 at least a subset of the images for display on a client device 110 (of a provider) different than the client devices 110 of the users. The exercise feedback system 100 can provide the subset of the images to be displayed in an order according to the scores of the corresponding user. For instance, images (or other content) for users having scores indicating a greater level of urgency are displayed on the top of a user interface (e.g., the central feed shown in FIG. 6) or presented more prominently than content for users having scores indicating a lower level of urgency, e.g., using bolded text or different colors. The exercise feedback system 100 receives 1050 from the client device 110, feedback describing the musculoskeletal form of the users responsive to providing the subset of the images for display. In an embodiment, the exercise feedback system 100 receives, as part of the feedback, one or more classifications (e.g., proper or improper) of musculoskeletal form of the subset of the images. Further, the exercise feedback system 100 may store the one or more classifications along with corresponding images of the subset in the user data store 230.

FIG. 11 is a flowchart illustrating a process 1100 for starting an exercise program using an augmented reality graphic according to one embodiment. In some embodiments, the process 1100 is performed by a client device 110 (including local components of the exercise feedback system 100) within the system environment in FIG. 1. The process 1100 may include different or additional steps than those described in conjunction with FIG. 11 in some embodiments or perform steps in different orders than the order described in conjunction with FIG. 11.

In an embodiment, the local AR engine 350 (shown in FIG. 3) of a client device 110 of a user provides 1110 an augmented reality (AR) graphic for display on the client device 110, where the AR graphic indicates a target musculoskeletal form for an exercise. The local exercise engine 320 receives 1120 video data captured by a camera of the client device 110. The camera is positioned such that the user is within a field of view of the camera. The client device 110 determines 1130 a musculoskeletal form of the user by processing the video data using the local data processing engine 335. The client device 110 determines 1140 a level of similarity between the musculoskeletal form and the target musculoskeletal form using the local data processing engine 335. Responsive to the local data processing engine 335 determining that the level of similarity satisfies a criteria, the local exercise engine 320 starts 1150 an exercise program for the exercise and provides a notification for display on the client device 110 indicating that the exercise program has started.

In another embodiment, the exercise feedback system 100 provides an AR graphic for display on a client device 110 of a user, where the AR graphic indicating a target musculoskeletal form for an exercise. The exercise feedback system 100 receives from the client device 110 video data captured by a camera of the client device 110. The exercise feedback system 100 determines a musculoskeletal form of the user by processing the video data. The exercise feedback system 100 provides an indication to the client device 110 that a level of similarity between the musculoskeletal form of the user and the target musculoskeletal form satisfies a criteria. In addition, the client device 110 is configured to start an exercise program for the exercise responsive to receiving the indication.

Alternative Embodiments

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving a classification of musculoskeletal form input by each of a plurality of human providers;

determining a level of quality of classification for each of the plurality of human providers by comparing each classification to a known set of proper classifications of musculoskeletal form;

determining a subset of the plurality of human providers by filtering out at least one of the plurality of human providers having a level of quality of classification less than a threshold value;

selecting a human provider from the subset of the plurality of human providers;

receiving, by an exercise feedback system from a first client device of a user, a set of one or more images captured by a camera of the first client device, the set of images indicating a musculoskeletal form of the user while performing an exercise;

sending, by the exercise feedback system to a second client device of the selected human provider, at least one image of the set of images for display to the selected human provider;

receiving, by the exercise feedback system from the second client device, a classification of the musculoskeletal form of the user, wherein the classification is input by the selected human provider responsive to viewing the at least one image of the set of images displayed by the second client device;

generating feedback for the exercise using at least the classification; and sending, by the exercise feedback system to the first client device, the feedback for display to the user.

2. The method of claim 1, further comprising:

sending, the one or more images for display on the first client device;

receiving, from the first client device, a selection of the at least one image of the set of images to be sent to the second client device.

3. The method of claim 1, further comprising:

receiving a first plurality of images captured by client devices of a first plurality of users including at least the user, each of the first plurality of images indicating musculoskeletal form of one of the first plurality of users while performing the exercise;

receiving a second plurality of images captured by client devices of a second plurality of users who did not perform the exercise, each of the second plurality of images indicating musculoskeletal form of one of the second plurality of users while not performing the exercise; and determining, using the first plurality of images and the second plurality of images, that one or more health metrics of the first plurality of users improved relative to one or more health metrics of the second plurality of users.

4. The method of claim 3, wherein determining that the one or more health metrics of the first plurality of users improved comprises:

determining a target musculoskeletal form for the exercise, the target musculoskeletal form indicating at least a target angle between a first segment and a second segment of a body of a given user while performing at least a portion of the exercise.

5. The method of claim 3, further comprising:

determining the first plurality of users and the second plurality of users from a population of users of the exercise feedback system using at least one of demographic information or physiological information of the population of users.

6. The method of claim 1, further comprising:

receiving a first set of classifications provided by a first set of physical trainers;

receiving a second set of classifications provided by a second set of physical trainers; and generating scores for the first and second sets of physical trainers using the comparison of the first set of classifications and the second set of classifications, each score indicating a metric of one of the classifications provided by the corresponding physical trainer.

7. The method of claim 6, further comprising:

receiving user information from a third client device of a new user of the exercise feedback system;

determining one or more candidate physical trainers of the first or second set of physical trainers using the scores; and displaying, by the third client device to the new user, information describing the one or more candidate physical trainers.

8. The method of claim 7, further comprising:

determining at least one preference of the new user using the user information, wherein the one or more candidate physical trainers is determined further by comparing the at least one preference with attributes of the first or second set of physical trainers.

9. The method of claim 1, further comprising:

labeling, responsive to receiving the classification, an image of the at least one image of the set of images as indicative of proper or improper musculoskeletal form for the exercise; and providing the feedback by displaying the labeled image on the first client device.

10. The method of claim 1, wherein the classification indicates a score of the musculoskeletal form of the user, the feedback indicating a trend in scores for historical musculoskeletal forms of the user.

11. The method of claim 1, wherein the camera and an electronic display are positioned on a same side of the first client device, and wherein the feedback is displayed on the electronic display while the user is performing the exercise.

12. The method of claim 1, wherein the camera includes at least a depth sensor configured to capture 3D images.

13. The method of claim 1, wherein the user is performing an exercise program including a plurality of repetitions of the exercise, the set of one or more images including images corresponding to different repetitions, the method further comprising:

providing, to the second client device, a duration of time that the user took to complete the plurality of repetitions of the exercise.

14. A non-transitory computer-readable storage medium storing instructions that when executed by a processor cause the processor to perform steps including:

receiving a classification of musculoskeletal form input by each of a plurality of human providers;

determining a level of quality of classification for each of the plurality of human providers by comparing each classification to a known set of proper classifications of musculoskeletal form;

determining a subset of the plurality of human providers by filtering out at least one of the plurality of human providers having a level of quality of classification less than a threshold value;

selecting a human provider from the subset of the plurality of human providers;

receiving, by an exercise feedback system from a first client device of a user, a set of one or more images captured by a camera of the first client device, the set of images indicating musculoskeletal form of the user while performing an exercise;

sending, by the exercise feedback system to a second client device of the selected human provider, at least one image of the set of images for display to the selected human provider;

receiving, by the exercise feedback system from the second client device, a classification of the musculoskeletal form of the user, wherein the classification is input by the selected human provider responsive to viewing the at least one image of the set of images displayed by the second client device;

generating feedback for the exercise using at least the classification; and sending, by the exercise feedback system to the first client device, the feedback for display to the user.

15. The computer-readable storage medium of claim 14, wherein the steps further comprise:

sending, the one or more images for display on the first client device;

receiving, from the first client device, a selection of the at least one image of the set of images to be sent to the second client device.

16. The computer-readable storage medium of claim 14, wherein the steps further comprise:

receiving a first plurality of images captured by client devices of a first plurality of users including at least the user, each of the first plurality of images indicating musculoskeletal form of one of the first plurality of users while performing the exercise;

receiving a second plurality of images captured by client devices of a second plurality of users who did not perform the exercise, each of the second plurality of images indicating musculoskeletal form of one of the second plurality of users while not performing the exercise; and determining, using the first plurality of images and the second plurality of images, that one or more health metrics of the first plurality of users improved relative to one or more health metrics of the second plurality of users.

17. The computer-readable storage medium of claim 16, wherein determining that the one or more health metrics of the first plurality of users improved comprises:

determining a target musculoskeletal form for the exercise, the target musculoskeletal form indicating at least a target angle between a first segment and a second segment of a body of a given user while performing at least a portion of the exercise.

18. The computer-readable storage medium of claim 16, wherein the steps further comprise:

determining the first plurality of users and the second plurality of users from a population of users of the exercise feedback system using at least one of demographic information or physiological information of the population of users.

19. The computer-readable storage medium of claim 14, wherein the steps further comprise:

receiving a first set of classifications provided by a first set of physical trainers;

receiving a second set of classifications provided by a second set of physical trainers; and generating scores for the first and second sets of physical trainers using the comparison of the first set of classifications and the second set of classifications, each score indicating a metric of one of the classifications provided by the corresponding physical trainer.

20. The computer-readable storage medium of claim 19, wherein the steps further comprise:

receiving user information from a third client device of a new user of the exercise feedback system;

determining one or more candidate physical trainers of the first or second set of physical trainers using the scores; and displaying, by the third client device to the new user, information describing the one or more candidate physical trainers.

* * * * *